United States Patent
Kirschbaum et al.

(10) Patent No.: US 7,629,493 B2
(45) Date of Patent: Dec. 8, 2009

(54) PROCESS FOR THE CRYSTALLISATION OF GUANDINIUM SALTS

(75) Inventors: Michael Kirschbaum, Weiterstadt (DE); Ekkehard Bartmann, Erzhausen (DE); Dieter Bensinger, Darmstadt (DE); Alexander Haas, Darmstadt (DE); Ricky Lippert, Brensbach (DE)

(73) Assignee: Merck Patent GmbH, Darmstadt (DE)

( * ) Notice: Subject to any disclaimer, the term of this patent is extended or adjusted under 35 U.S.C. 154(b) by 356 days.

(21) Appl. No.: 10/555,789

(22) PCT Filed: Apr. 10, 2004

(86) PCT No.: PCT/EP2004/003838

§ 371 (c)(1),
(2), (4) Date: Nov. 4, 2005

(87) PCT Pub. No.: WO2004/099125

PCT Pub. Date: Nov. 18, 2004

(65) Prior Publication Data

US 2007/0055064 A1 Mar. 8, 2007

(30) Foreign Application Priority Data

May 6, 2003 (DE) ................. 103 20 016

(51) Int. Cl.
*C07C 233/65* (2006.01)

(52) U.S. Cl. .............. 564/162; 564/237; 564/163; 564/164; 548/561; 544/392; 544/393

(58) Field of Classification Search ............ 564/237, 564/164, 163, 162; 548/561; 544/392, 393
See application file for complete search history.

(56) References Cited

U.S. PATENT DOCUMENTS

| 3,975,533 A | 8/1976 | Kodama et al. |
| 4,113,776 A * | 9/1978 | Cohen et al. ............. 564/238 |
| 5,744,641 A | 4/1998 | Gericke et al. |
| 5,840,761 A | 11/1998 | Baumgarth et al. |
| 6,147,098 A * | 11/2000 | Mogensen et al. ........ 514/357 |
| 6,673,968 B1 * | 1/2004 | Gericke et al. ............ 564/237 |

FOREIGN PATENT DOCUMENTS

EP 0 758 644 A 2/1997

* cited by examiner

*Primary Examiner*—Shailendra Kumar
(74) *Attorney, Agent, or Firm*—Millen, White, Zelano, Branigan, P.C.

(57) ABSTRACT

The invention relates to a process for the crystallization of the compounds of the formula (I) or acid-addition salts thereof, in which $R^1$, $R^2$ and $R^3$ have the meaning indicated in Claim 1.

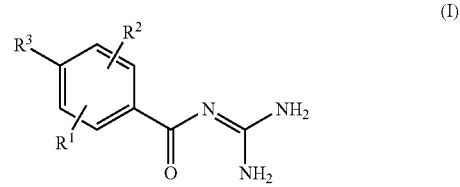

(I)

17 Claims, No Drawings

PROCESS FOR THE CRYSTALLISATION OF GUANDINIUM SALTS

This application is a 371 of PCT/EP04/03838, filed Apr. 10, 2004.

The invention relates to a process for the crystallisation of the compounds of the formula I or acid-addition salts thereof,

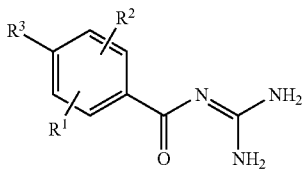

in which
$R^1$ $R^4SO_2$— or A,
$R^2$ and $R^3$, independently of one another, H, Hal, alkyl having 1 to 12 C atoms, $R^4SO_2$—, Ar or Het,
$R^4$ aryl or alkyl having 1 to 12 C atoms,
Het a saturated, unsaturated or aromatic, mono- or bicyclic, heterocyclic or linear or branched organic radical containing one or more hetero atoms which is unsubstituted or mono- or polysubstituted by A, COAr, COHet and/or Hal,
Ar a phenyl radical which is unsubstituted or mono- or polysubstituted by A and/or Hal, OH, OA, COOH, COOA, $CONH_2$, $CONA_2$, CONHA, CN, $NO_2$, $NH_2$, NHA, $NA_2$, NHCOA, $CF_3$ or $SO_2A$,
A straight-chain or branched alkyl or hydroxyalkyl having 1 to 10 C atoms, alkenyl or alkoxyalkyl having 2 to 10 C atoms, and
Hal F, Cl, Br, I characterised in that the respective compounds of the formula I or mixtures thereof with impurities are dissolved at a given temperature in water which is virtually saturated with at least one water-immiscible solvent and optionally comprises one or more water-miscible solvents, and the compounds of the formula I are allowed to crystallise at a lower temperature.

The compounds of the formula I can have one or more chiral centres. They can accordingly occur in various enantiomeric forms and exist in racemic or in optically active form. The invention therefore also relates to the optically active forms (stereoisomers), the enantiomers, the racemates, the diastereomers and hydrates and solvates of these compounds. The tautomeric forms of the compounds of the formula I are also in accordance with the invention.

Sulfonylbenzoylguanidines are known and are described, for example, in EP 0 758 644 A1. These substances are inhibitors of the cellular $Na^+/H^+$ antiproter, i.e. active ingredients which inhibit the Na+/H+ exchange mechanism of the cells (Düsing et al., Med. Klin. 1992,87,367-384) and are thus good antiarrhythmics which are suitable, in particular, for the treatment of arrhythmia arising as a consequence of oxygen deficiency.

These substances exhibit a good cardioprotective action and are therefore particularly suitable for the treatment of acute myocardial infarction, infarction prophylaxis, post-infarction treatment, chronic cardiac insufficiency and for the treatment of angina pectoris. They furthermore counter all pathological hypoxic and ischaemic damage, enabling the treatment of diseases caused primarily or secondarily thereby. These active ingredients are likewise highly suitable for preventive applications.

Owing to the protective action of these substances in pathological hypoxic or ischaemic situations, further potential applications result therefrom in surgical interventions for the protection of temporarily undersupplied organs, in organ transplants for protection of the removed organs, in angioplastic vascular or cardiac interventions, in ischaemia of the nervous system, in the therapy of shock states and for the prevention of essential hypertonia.

These compounds can furthermore also be employed as therapeutic agents in diseases caused by cell proliferation, such as arteriosclerosis, diabetes and late complications of diabetes, tumour diseases, fibrotic diseases, in particular of lung, liver and kidneys, and organ hypertrophy and hyperplasia. In addition, the compounds are suitable for diagnostic use for the recognition of diseases accompanied by increased activity of the $Na^+/H^+$ antiporter, for example in erythrocytes, thrombocytes or leukocytes.

The compounds can therefore be used medicament active ingredients in human and veterinary medicine. They can furthermore be used as intermediates for the preparation of further medicament active ingredients.

Compounds of the formula I can be prepared, for example, in accordance with EP 0 758 644. In these processes, the active ingredients are usually obtained with a content of 95 to 99 HPLC area per cent, which does not meet the requirements of pharmaceutical active ingredients. An additional purification operation is necessary.

However, recrystallisation of the products from water or conventional organic solvents is virtually impossible. Besides the only low solubility of the products (even at elevated temp.), which cause poor crystallisation yields, crystals of inadequate purity are obtained. Even repeated crystallisation from water or conventional organic solvents does not result in material of adequate purity.

It is possible to achieve purification of the crude product by dissolution in copious water and subsequent concentration of the aqueous solution under reduced pressure to a fraction of the original volume, during which the product crystallises out. The disadvantage of this process are the very long process duration (the concentration of aqueous solutions requires a number of days in the case of large batches) and the consequent product losses due to hydrolysis.

The object of the present invention was therefore to provide an improved crystallisation process for the compounds of the formula I and acid-addition salts thereof which can be used on large industrial scales.

This object has been achieved by the process according to the invention for the crystallisation of the compounds of the formula 1, which is characterised in that the respective compounds of the formula I or mixtures thereof with impurities are dissolved at a given temperature in water which is virtually saturated with at least one water-immiscible solvent and optionally comprises one or more water-miscible solvents, and the compounds of the formula I are allowed to crystallise at a lower temperature.

In the compounds of the formulae 1, the radicals have the following preferred meanings:

$R^1$ preferably denotes $R^4SO_2$— or A.

$R^2$ in the compounds of the formula I is preferably in the ortho-position to the guanidine radical and preferably denotes H or alkyl having 1 to 7 C atoms, in particular H or methyl.

$R^3$ preferably denotes H, alkyl having 1 to 7 C atoms, $R^4SO^2$— or Het, in particular $R^4SO_2$— or Het.

$R^4$ preferably denotes phenyl, m-, o- or p-tolyl or methyl, ethyl, isopropyl, n-butyl or n-pentyl. Particular preference is given to methyl or ethyl, in particular methyl.

Ar preferably denotes phenyl, m- o- or p-methyl or methoxyphenyl.

Het preferably denotes

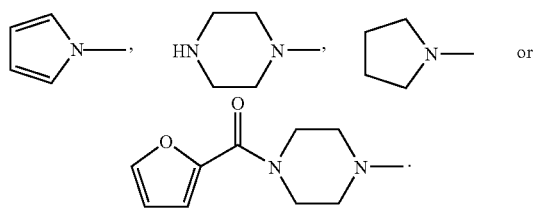

Hal preferably denotes Cl or Br, in particular F or Cl.

The process according to the invention is particularly suitable for the crystallisation of compounds of the formula Ia to Ie or acid-addition salts thereof:

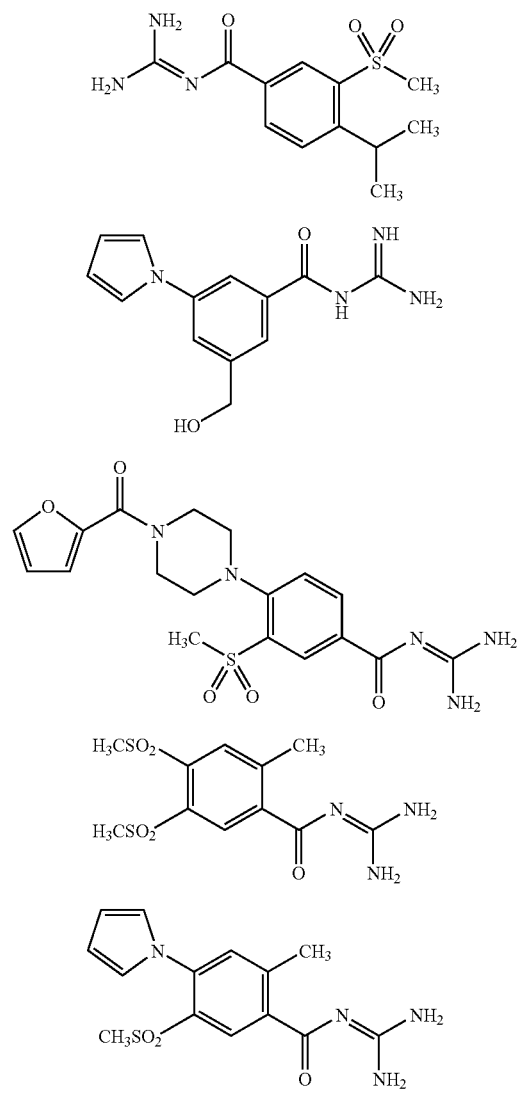

The reaction of the process according to the invention is simple to carry out, where the compounds of the formula I can be recrystallised if the solvent used is water which is virtually saturated with a water-immiscible solvent. This is entirely unexpected since the solubility of the compounds of the formula I in the pure solvents, i.e. in water or in one or more water-immiscible solvents, is inadequate to facilitate effective recrystallisation. With the solvent system according to the invention, however, an excellent space-time yield can be achieved at the same time as very good purity (>99.7 HPLC area per cent), even in the case of large batches.

For practical performances, it is not necessary to set the saturation mixing ratio of the two solvents precisely. An excess of water-immiscible solvent is preferably used. After dissolution of the product in the solvent mixture at elevated temperatures, the excess water-immiscible solvent is preferably separated off, and the solution is allowed to cool in order to crystallise out. Since the incomplete removal of the excess water-immiscible solvent does not have an adverse effect on the crystallisation, crystallisation can also be carried out directly from the two-phase mixture.

Suitable water-immiscible solvents for the process according to the invention are generally all known solvents which are immiscible with water to a first approximation. These are preferably relatively long-chain water-immiscible ketones, such as, for example, methyl ethyl ketone, or alkyl alkanoates, such as, for example, ethyl acetate, isopropyl acetate, methyl acetate or ethyl propionate. Furthermore, aromatic solvents or higher alcohols, such as, for example, butanol, can preferably be used. Particular preference is given to toluene or xylene. After comparison of all relevant parameters (yield, purity, price, environmental acceptability, etc.), however, alkyl alkanoates, in particular ethyl acetate, are preferred to other solvents.

The process according to the invention can be further refined in practical application if multicomponent mixtures are used. Preference is given to a mixture of water, a water-immiscible solvent and an alcohol, in particular a mixture of water, ethanol and ethyl acetate. Preferred concentration ranges are those in which the alcohol added to the solvent mixture does not promote complete miscibility of water and water-immiscible solvent.

Alcohols which can be used are particularly preferably ethanol, methanol or n- or isopropanol.

Instead of the alcohol, it is also possible to use ketones and nitriles. Preference is given to water-soluble ketones, in particular acetone.

The compounds of the formula I are preferably dissolved in the respective solvent mixture at elevated temperatures, preferably at 30-180° C., in particular at 60-100° C. and very particularly preferably at 60-70° C., and brought to crystallisation at lower temperatures, preferably at room temperature.

The duration of the reaction of the crystallisation depends on the reaction conditions selected. In general, the crystallisation duration is 0.5 hours to 2 days, preferably 1 to 15 hours.

In a preferred embodiment of the crystallisation process according to the invention, the pH is adjusted to 1 to 3.5, in particular 1 to 2, with the aid of a suitable acid (for example using HCl in the case of hydrochlorides, using methanesulfonic acids in the case of methanesulfonate) before or during the crystallisation.

Acids which are added before or during the crystallisation are furthermore those which form physiologically acceptable and tolerated salts with the compounds of the formula I.

Preference may be given for this purpose to the use of inorganic acids, for example sulfuric acid, nitric acid, hydrohalic acids, such as hydrochloric acid or hydrobromic acid, phosphoric acids, such as orthophosphoric acid, sulfamic acid, furthermore organic acids, in particular aliphatic, alicyclic, araliphatic, aromatic or heterocyclic mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and disulfonic acids, laurylsulfuric acid.

Particular preference is given to hydrochloric acid or methanesulfonic acid.

The amounts of the solvent mixtures for the crystallisation according to the invention is not crucial, 10 g to 500 g of solvent mixtures per g of the compounds of the formula I to be dissolved can preferably be used.

Even without further embodiments, it is assumed that a person skilled in the art will be able to utilise the above description in the broadest scope. The preferred embodiments should therefore merely be regarded as descriptive disclosure which is absolutely not limiting in any way.

The following examples are intended to explain the invention without limiting it. Unless stated otherwise, percentages denote per cent by weight. All temperatures are indicated in degrees Celsius.

EXAMPLE 1

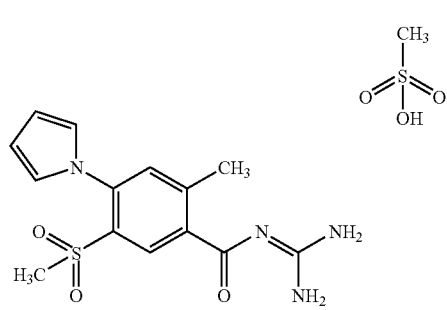

30.00 g of compound 1 to be purified and 300 ml of ethyl acetate are added to 550 ml of water with stirring at about 73° C. The mixture is stirred at 75° C. for 40 min., with two clear phases forming. The aqueous phase is separated off and passed through a steam-heated 2 l Seitz filter (filter K 900). The aqueous phase is allowed to cool overnight with stirring and is stirred for a further 3 hours with ice-cooling. The crystals formed are separated off, rinsed with cold water and dried at 50° C., giving compound 1 in a purity of 99.9%.

EXAMPLE 2

65 g of contaminated compound 1 from Example 1 and 300 ml of ethyl acetate are added to a mixture of 550 ml of water and 100 ml of ethanol at 71° C. The mixture is stirred at 70° C. for 30 minutes, with two clear phases forming. The aqueous phase is separated off and filtered through a steam-heated Seitz filter (Beco SD30). The pH is adjusted to 1.5 by addition of 1.5 g of methanesulfonic acid. The aqueous phase is allowed to cool overnight with stirring and is stirred for a further 3 hours with ice-cooling. The crystals formed are separated off, rinsed with cold water and dried at 50° C., giving compound I in a purity of 99.9% and in improved yield compared with Example 1.

EXAMPLE 3

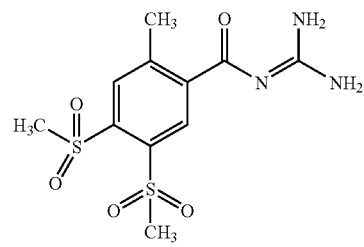

17.80 g of compound 2 to be purified and 454 ml of ethyl acetate are added to 182 ml of water with stirring at about 70° C. The mixture is stirred at 65° C. for 40 minutes, with two clear phases forming. The aqueous phase is separated off and adjusted to pH 1.0 using aqueous hydrochloric acid. The aqueous phase is allowed to cool overnight with stirring and is stirred for a further 3 hours with ice-cooling. The crystals formed are separated off, rinsed with cold water and dried at 50° C., giving compound 2 in the form of its hydrate in a purity of 99.9%.

EXAMPLE 4

35.80 g of compound 2 to be purified and 456 ml of ethyl acetate are added to 501 ml of water with stirring at about 70° C. The mixture is stirred at 65° C. for 40 minutes, with two clear phases forming. The aqueous phase is separated off and adjusted to pH 1.4 using aqueous hydrochloric acid. The aqueous phase is allowed to cool overnight with stirring and is stirred for a further 3 hours with ice-cooling. The crystals formed are separated off, rinsed with cold water and dried at 50° C., giving compound 2 in the form of its hydrate in a purity of 99.9%.

EXAMPLE 5

40.00 g of compound 2 to be purified and 113.2 g of ethyl acetate are added to a mixture of 282 ml of water and 51.7 g of ethanol with stirring at about 70° C. The mixture is stirred at about 65° C. for 10 minutes, with two phases forming. A further 30.00 g of compound 2 to be purified are subsequently introduced over the course of 15 minutes with stirring. The aqueous phase is separated off and adjusted to pH 1.2 using aqueous hydrochloric acid. The aqueous phase is allowed to cool and is stirred for a further 1 hour with ice-cooling. The crystals formed are separated off, rinsed with cold water and dried at 50° C., giving compound 2 in the form of its hydrate in a purity of 99.9%.

The invention claimed is:
1. A process for the crystallisation of a compound of formula I or an acid-addition salt thereof,

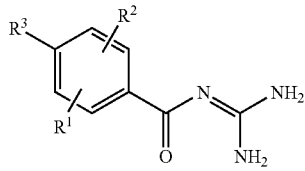

in which

R¹ R⁴SO₂— or A,

R² and R³, independently of one another, H, Hal, alkyl having 1 to 12 C atoms, R¹SO₂—, Ar or Het, R⁴ aryl or alkyl having 1 to 12 C atoms, Het a saturated, unsaturated or aromatic, mono- or bicyclic, heterocyclic or linear or branched organic radical containing one or more hetero atoms which is unsubstituted or mono- or polysubstituted by A, COAr, COHet and/or Hal, Ar a phenyl radical which is unsubstituted or mono- or polysubstituted by A and/or Hal, OH, OA, COOH, COOA, CONH₂, CONA₂, CONHA, CN, NO₂, NH₂, NHA, NA₂, NHCOA, CF₃ or SO₂A, A straight-chain or branched alkyl or hydroxyalkyl having 1 to 10 C atoms, alkenyl or alkoxyalkyl having 2 to 10 C atoms, and Hal F, Cl, Br, I comprising dissolving the respective compound of formula I, optionally with impurities, at a given dissolution temperature in water which is virtually saturated with at least one water-immiscible solvent and optionally comprises one or more water-miscible solvents, and allowing the compound of formula I to crystallise at a temperature that is lower then said dissolution temperature, and wherein the water-immiscible solvent is an alkyl alkanoate or an aromatic solvent.

2. A process according to claim 1 for the crystallisation of a compound of formula Ia to Ie

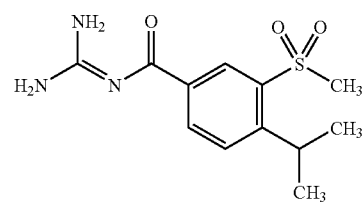

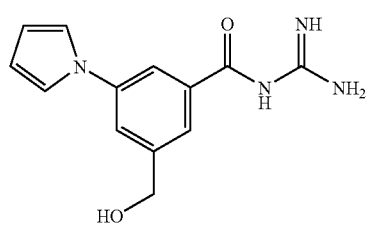

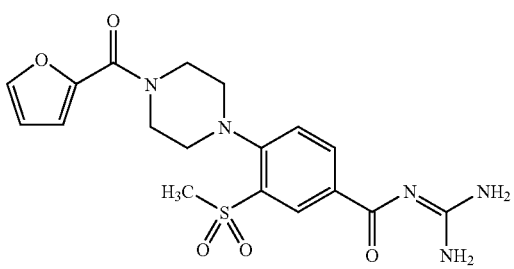

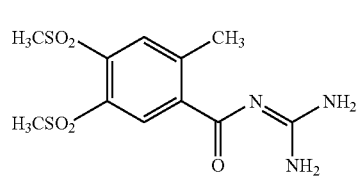

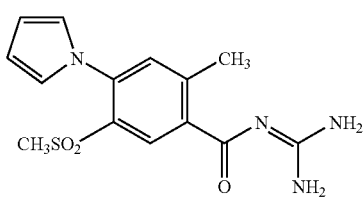

or acid-addition salt thereof.

3. A Process according to claim 1, wherein an excess of water-immiscible solvent is employed.

4. A process according to claim 1, wherein a mixture of water, one or more water-immiscible solvent and one or more alcohols is used.

5. A process according to claim 4, wherein the alcohol used is ethanol, methanol or nor isopropanol.

6. A process according to claim 4, wherein the alcohol used is added to the solvent mixture in amounts in which it does not promote complete miscibility of water and water-immiscible solvent.

7. A process according to claim 1, wherein the pH is adjusted to 1 to 3.5 with the aid of a suitable acid before or during the crystallisation.

8. A process according to claim 1, wherein R² is in the ortho-position to the guanidine radical.

9. A process to claim 8, wherein R² is H or a $C_{1-7}$ alkyl.

10. A process according to claim 1 wherein R³ is R⁴SO₂— or Het.

11. A process according to claim 1, wherein R⁴ is methyl or ethyl.

12. A process according to claim 1, wherein Ar is phenyl, m- o- or p-methyl or methoxyphenyl.

13. A process according to claim 1, wherein Hal is F or Cl.

14. A process according to claim 1, wherein Het is

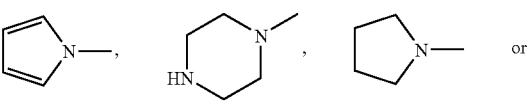

-continued

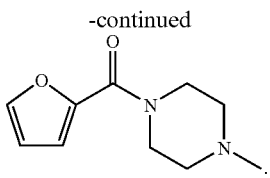

15. A process according to claim 1, wherein said alkyl alkanoate is ethyl acetate, isopropyl acetate, methyl acetate or ethyl propionate.

16. A process according to claim 1, wherein said compound of formula I is dissolved in the solvent mixture at about 60-100° C. and brought to crystallisation at about room temperature.

17. A process according to claim 16, wherein compounds of formula I are dissolved in the solvent mixture at about 60-100° C. and brought to crystallisation at about room temperature.

* * * * *

UNITED STATES PATENT AND TRADEMARK OFFICE
CERTIFICATE OF CORRECTION

| | |
|---|---|
| PATENT NO. | : 7,629,493 B2 |
| APPLICATION NO. | : 10/555789 |
| DATED | : December 8, 2009 |
| INVENTOR(S) | : Kirschbaum et al. |

Page 1 of 1

It is certified that error appears in the above-identified patent and that said Letters Patent is hereby corrected as shown below:

Column 8, line 40, reads "A process according to claim 4, wherein the alcohol used" should read -- A process according to claim 4, wherein the alcohol --.

Column 10, line 8 reads "60-100°C. and brought to crystallisation at about room tem-" should read -- 60-70°C. and brought to crystallisation at about room tem- --

Signed and Sealed this

Sixteenth Day of February, 2010

David J. Kappos
*Director of the United States Patent and Trademark Office*

UNITED STATES PATENT AND TRADEMARK OFFICE
CERTIFICATE OF CORRECTION

PATENT NO. : 7,629,493 B2
APPLICATION NO. : 10/555789
DATED : December 8, 2009
INVENTOR(S) : Kirschbaum et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 360 days.

Signed and Sealed this

Second Day of November, 2010

David J. Kappos
*Director of the United States Patent and Trademark Office*